United States Patent [19]
Golds et al.

[11] Patent Number: 5,356,412
[45] Date of Patent: Oct. 18, 1994

[54] STERNUM BUCKLE WITH ROTATIONAL ENGAGEMENT AND METHOD OF CLOSURE

[75] Inventors: Ellen M. Golds, Hastings-on-Hudson, N.Y.; Ross R. Muth, Brookfield, Conn.

[73] Assignee: United States Surgical Corporation, Norwalk, Conn.

[21] Appl. No.: 959,051

[22] Filed: Oct. 9, 1992

[51] Int. Cl.⁵ .............................................. A61B 17/00
[52] U.S. Cl. ........................................ 606/74; 606/72; 606/151; 24/170
[58] Field of Search .................... 606/1, 60, 72, 74, 86, 606/87, 105, 139, 148, 151, 213, 215, 216–218, 232; 128/898; 24/170, 191

[56] References Cited

U.S. PATENT DOCUMENTS

| | | |
|---|---|---|
| 1,717,766 | 6/1929 | Eimler . |
| 1,950,799 | 3/1934 | Jones . |
| 2,622,292 | 12/1952 | Pehaczek . |
| 2,948,939 | 8/1960 | Prete, Jr. . |
| 2,987,062 | 6/1961 | Ellison . |
| 3,111,945 | 11/1963 | Von Solbrig . |
| 3,469,573 | 9/1969 | Florio . |
| 3,473,528 | 10/1969 | Mishkin et al. . |
| 3,570,497 | 3/1971 | Lemole . |
| 3,577,601 | 5/1971 | Mariani . |
| 3,678,542 | 7/1972 | Prete, Jr. ................ 24/170 |
| 3,802,438 | 4/1974 | Wolvek . |
| 3,852,855 | 12/1974 | Bengtsson ............. 24/170 |
| 4,037,603 | 7/1977 | Wendorff . |
| 4,051,743 | 10/1977 | Gaylord .................. 24/170 |
| 4,119,091 | 10/1978 | Partridge . |
| 4,148,224 | 4/1979 | Craig ..................... 24/191 |
| 4,201,215 | 5/1980 | Crossett et al. . |
| 4,263,904 | 4/1981 | Judet . |
| 4,279,248 | 7/1981 | Gabbay . |
| 4,387,489 | 6/1983 | Dudek .................... 24/170 |
| 4,512,346 | 4/1985 | Lemole . |
| 4,535,764 | 8/1985 | Ebert . |
| 4,583,541 | 4/1986 | Barry . |
| 4,625,717 | 12/1986 | Covitz . |
| 4,643,178 | 2/1987 | Nastari et al. . |
| 4,667,662 | 5/1987 | Titone et al. . |
| 4,727,628 | 3/1988 | Rudholm ................ 24/170 |
| 4,730,615 | 3/1988 | Sutherland et al. . |
| 4,754,530 | 7/1988 | Lindblad . |
| 4,792,336 | 12/1988 | Hlavacek et al. . |
| 4,802,477 | 2/1989 | Gabbay . |
| 4,804,383 | 2/1989 | Rey et al. . |
| 4,813,416 | 3/1989 | Pollak et al. . |
| 4,878,271 | 11/1989 | Kitokovsky . |
| 4,896,668 | 1/1990 | Popoff et al. . |
| 4,920,959 | 5/1990 | Witzel et al. . |
| 4,943,292 | 7/1990 | Foux . |
| 4,944,753 | 7/1990 | Burgess et al. . |
| 4,955,913 | 9/1990 | Robinson . |
| 4,966,600 | 10/1990 | Songer et al. . |
| 5,024,618 | 6/1991 | Tepic . |
| 5,089,012 | 2/1992 | Prou . |
| 5,139,498 | 8/1992 | Ley . |
| 5,161,351 | 11/1992 | Woodruff ............... 24/170 |
| 5,163,598 | 11/1992 | Peters et al. . |
| 5,172,455 | 12/1992 | Johnson et al. ........ 24/191 |
| 5,207,694 | 5/1993 | Broomé .................. 606/151 |

FOREIGN PATENT DOCUMENTS

| | | |
|---|---|---|
| 2730571 | 1/1978 | Fed. Rep. of Germany . |
| 2824037 | 12/1979 | Fed. Rep. of Germany ........ 24/170 |
| 3042699 | 5/1981 | Fed. Rep. of Germany . |
| 3244680 | 6/1984 | Fed. Rep. of Germany . |
| 9210460 | 8/1992 | France . |
| WO90/06725 | 6/1990 | PCT Int'l Appl. ................ 604/264 |

*Primary Examiner*—Stephen C. Pellegrino
*Assistant Examiner*—Jeffrey A. Schmidt

[57] ABSTRACT

A strap assembly to be looped about split portions of human tissue to retain the split portions in adjacent contacting relation to promote healing thereof includes a flexible elongated member and a buckle member. The buckle member includes a frame member and a clamp member rotatably mounted within the frame member from a non-strap securing position to a strap securing position. The clamp member rotates to the strap securing position in response to tensional forces exerted on the strap during tensioning thereof about the tissue portions.

27 Claims, 5 Drawing Sheets

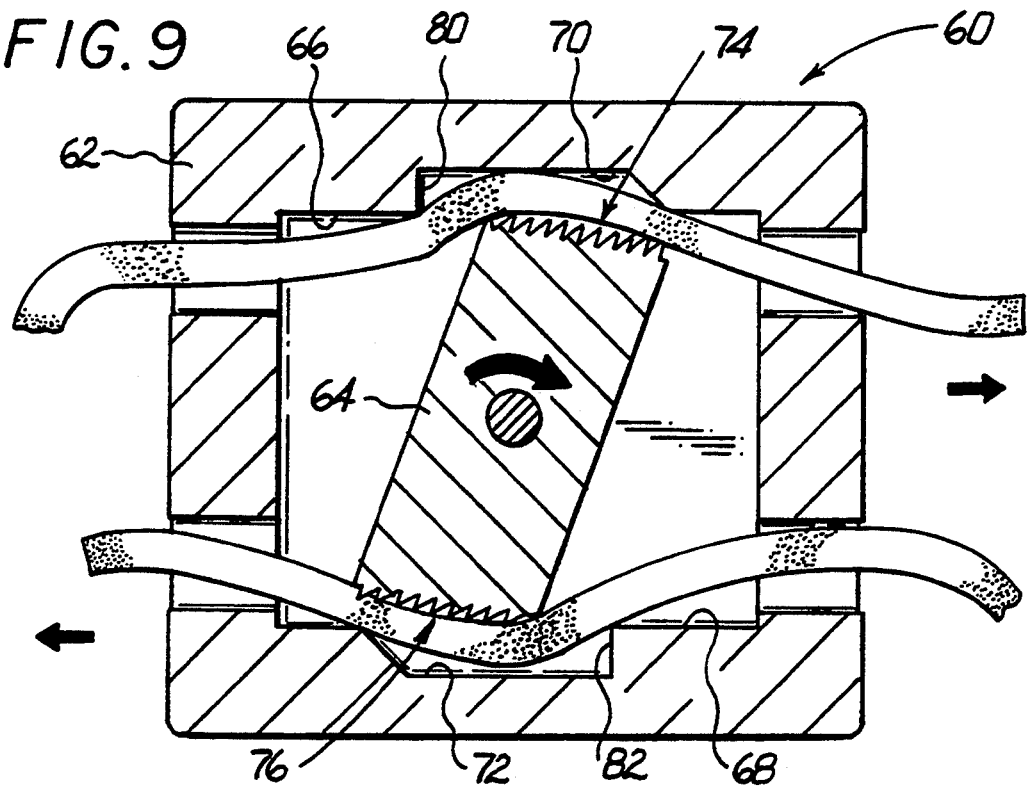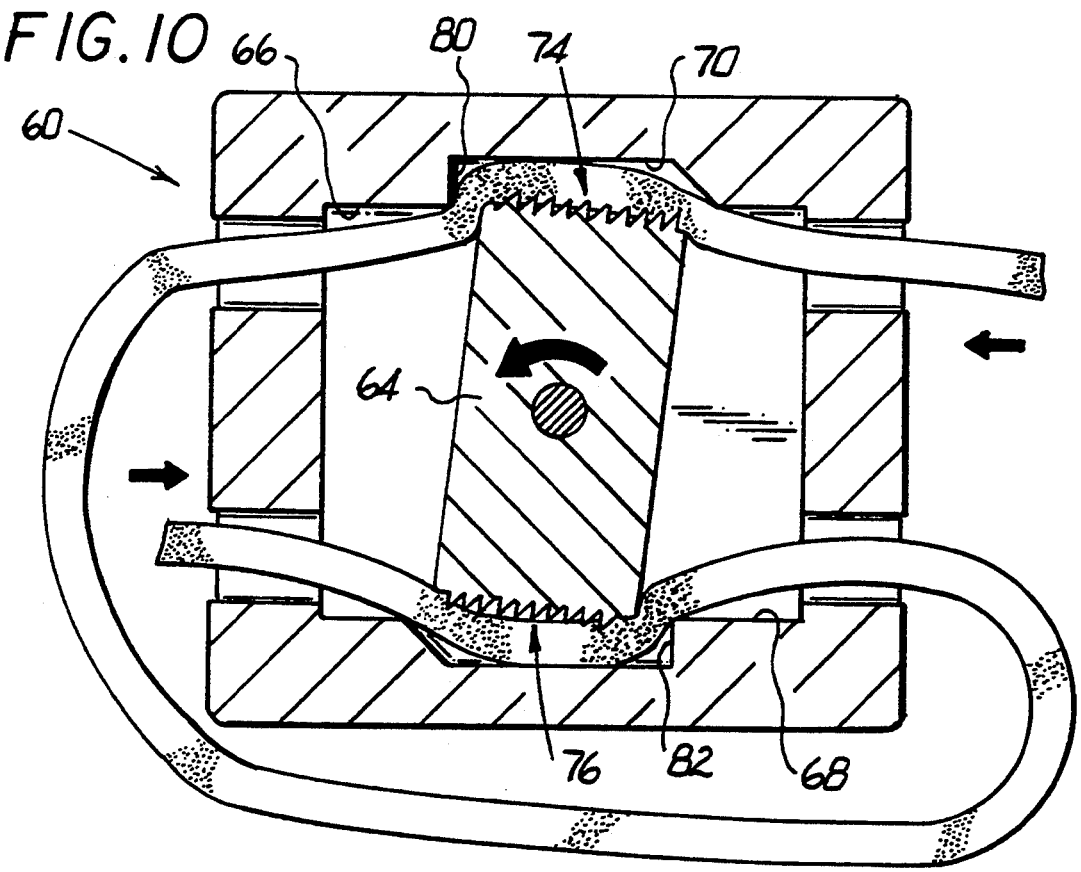

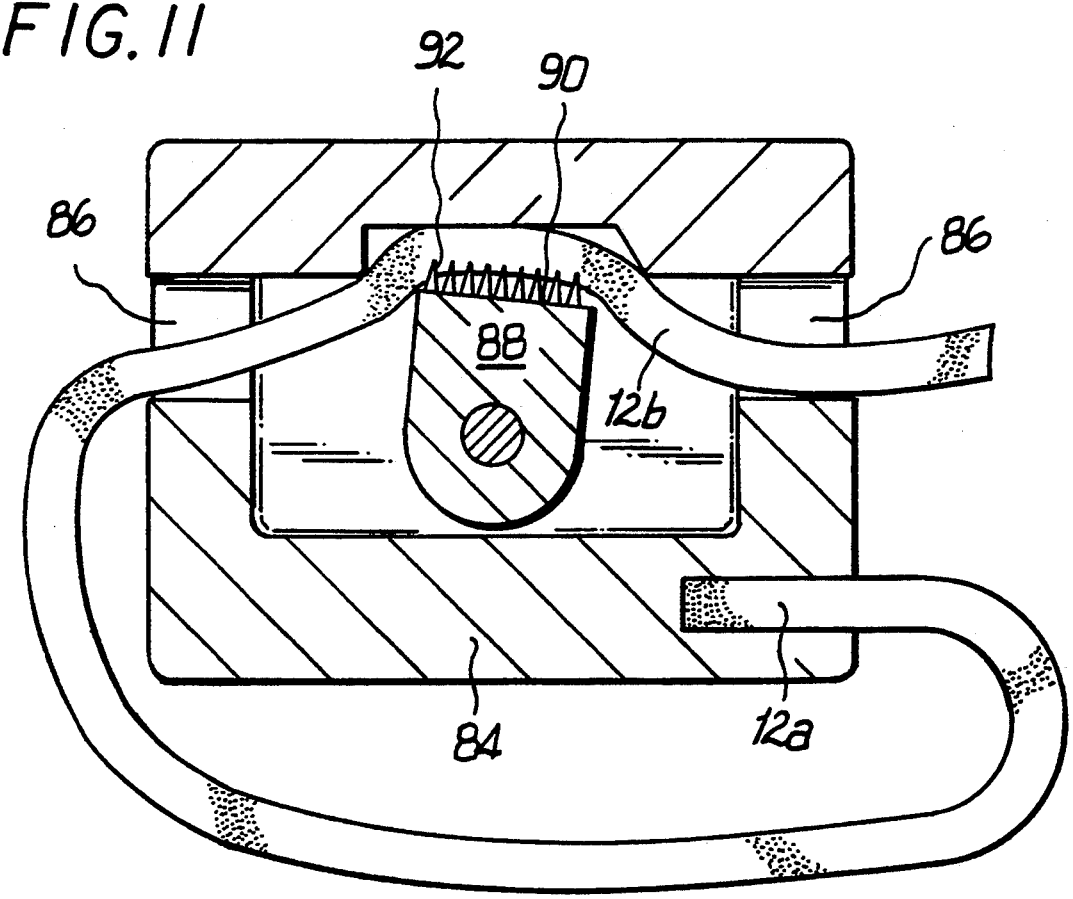

STERNUM BUCKLE WITH ROTATIONAL ENGAGEMENT AND METHOD OF CLOSURE

BACKGROUND OF THE INVENTION

1. Field of the Invention

The present invention relates to surgical devices for repair of split portions of tissue. In particular, the invention is directed to a strap assembly for securing a strap about split portions of a sternum to maintain the portions in adjacent contacting relationship during healing.

2. Description of the Prior Art

During surgery that involves a median sternotomy, e.g., open heart surgery, the sternum is split longitudinally to allow access to the organs within the thoracic cavity. Upon completion of the surgery, the sternum is rejoined and closed securely. For proper healing to occur, the split sternum portions are preferably engaged in face-to-face relationship and compressed together while the sternum heals.

Traditional methods for closing a sternum involve securing steel wires around or through the sternum halves and approximating the sternum by twisting the wires together.

Recently, a certain amount of emphasis has been directed towards the use of band or strap assemblies for sternum repair. Such assemblies typically include a locking mechanism which secures a strap in a closed looped configuration about the sternum portions. One example of an assembly of this type is described in U.S. Pat. No. 4,813,416 and includes a banding assembly having a curved surgical needle, an attached thin flat stainless steel band and a buckle mechanism. The sternum halves are brought to abutting closure by looping the band in position around or through the sternum portions and securing the band within the buckle mechanism.

While utilization of steel wires and strap assemblies have been widely accepted for sternum repair, certain shortcomings with these devices are apparent. The use of steel wires presents problems to the surgeon during the operation and to the patient after closure is completed. Steel wires are difficult to maneuver and place around the sternum. The wire edges are often sharp and can easily pierce through undesired areas including tissue surrounding the sternum area or the surgeon's gloves or fingers.

The strap assemblies known heretofore incorporate buckle mechanisms which are relatively structurally complex. For example, the buckle mechanism described in U.S. Pat. No. 4,813,416 includes a saddle part, interned flanges disposed on opposing sides of the saddle part and a loop segment. The saddle part and interned flanges define a band slide through course for reception of a portion of the band. A spring leaf extends upwardly from the loop segment through a slot in the saddle part. The tip end of the spring leaf is narrowed to define a spring tooth or projection which projects through an aperture formed in the band to maintain the closed band loop in a locked configuration.

Thus, there is a clear need for a surgical device which is simple in construction and effectively secures the divided sternum portions together for healing. The present invention is directed to a strap assembly having a buckle member of relatively simple construction which securably retains a strap in a closed looped locking configuration around sternum portions to maintain the portions in adjacent engaged relation during healing.

SUMMARY OF THE INVENTION

A strap assembly for surgical repair of split portions of tissue to retain the tissue portions in adjacent contacting relation during healing comprises a strap member and buckle means responsive to tensional forces exerted on the strap member for securing the strap member in a looped tensioned condition about the split tissue portions. The preferred buckle means comprises frame means which defines at least one longitudinal passageway for reception of the strap member and clamp means rotatably mounted within the frame means from a non-strap securing position to a strap securing position in response to the tensional forces exerted on the strap member during tensioning thereof about the tissue portions.

The clamp means defines at least one wedging surface which securely wedges the strap member against a bearing surface of the frame means when the clamp means is in the strap securing position. The wedging surface of the clamp means comprises strap engaging means for facilitating engagement of the strap member. The strap engaging means is preferably angularly oriented in a manner to permit advancement of the strap member through the passageway in a strap tightening direction while engaging the strap member when the strap member moves through the passageway in a strap loosening direction. Accordingly, engagement of the strap member with the clamp means during movement of the strap member in the strap loosening direction effects rotational movement of the clamp means to the strap securing position to securely wedge the strap member within the buckle means.

The strap engaging means preferably comprises engaging teeth formed on the wedging surface. Alternatively, the strap engaging means comprises piercing pins which may be mounted to the wedging surface by conventional means.

In a preferred embodiment, the strap assembly comprises a flexible strap member having first and second end portions and a buckle member. The buckle includes a frame member having a first longitudinal passageway for accommodating the first strap end portion and a second longitudinal passageway for accommodating the second strap end portion, and a clamp member. The clamp member is rotatably mounted within the frame member from a non-strap securing position to a strap securing position. In the non-strap securing position, the clamp member permits advancement of the first and second strap end portions in a tightening direction to tension the strap member about the tissue portions. In the tensioned condition the strap member generates clamping forces opposing the tensional forces exerted on the strap member during tensioning thereof. Accordingly, release of the strap end portions causes movement thereof in a loosening direction and engagement with the clamp member to effect rotational movement of the clamp member to the strap securing position.

The present invention is also directed to a method for repairing split portions of tissue. The method comprises the steps of providing a strap assembly including a strap member and buckle means, the buckle means including frame means defining at least one longitudinal passageway for reception of the strap member and clamp means rotatably mounted within the frame means from a non-strap securing position to a strap securing position in response to tensional forces exerted on the strap member during tensioning thereof, looping the strap member around the tissue portions, inserting the strap member through the one passageway in the buckle means, tightening the looped strap member about the tissue portions in a manner to attach the tissue portions in an adjacent engaged relation and securing the strap member to the buckle means.

The present invention is also directed to a method for repairing split sternum portions. In accordance with this preferred method, the strap member is looped about the sternum portions in a criss-cross manner through several parasternal locations. Thereafter, the strap member is secured at a predetermined location along the sternum, preferably with a buckle constructed according to the present invention.

BRIEF DESCRIPTION OF THE DRAWINGS

Preferred embodiments of the invention will be described hereinbelow with reference to the drawings wherein:

FIG. 9 is a side-view in cross-section of an alternative embodiment of the buckle member of the present invention;

FIG. 10 is a side view in cross-section of the buckle member of FIG. 9, illustrating the secured position of the buckle member with the clamp member securely engaging the strap received within the buckle; and FIG. 11 is a side view in cross-section of another alternative embodiment of the buckle member of the present invention.

DETAILED DESCRIPTION OF THE PREFERRED EMBODIMENT

Figure 1:
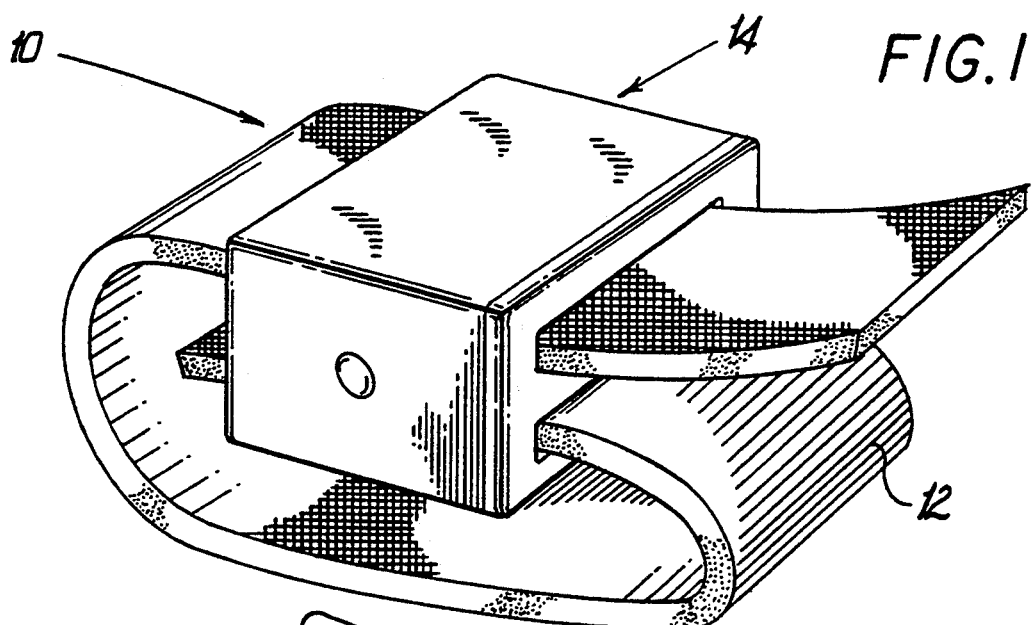
FIG. 1 is a perspective view of the strap assembly constructed according to the present invention illustrating the buckle member with attached strap.
Figure 2:
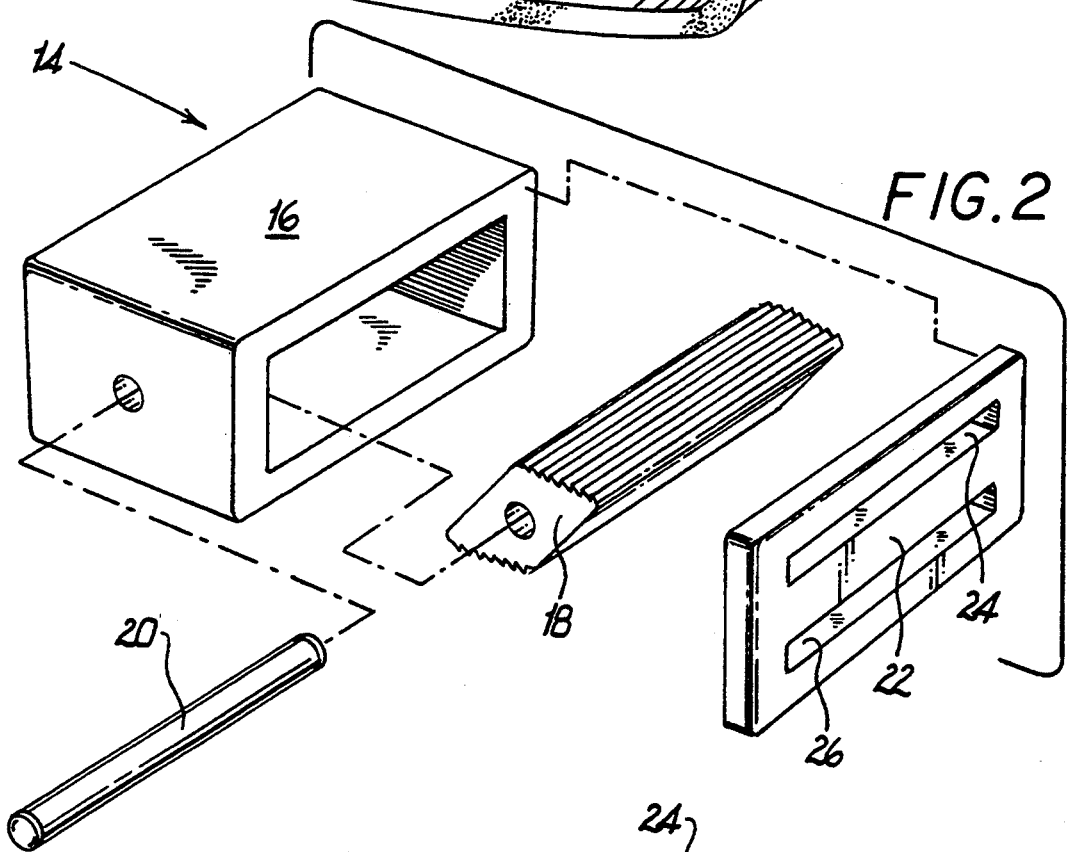
FIG. 2 is a perspective view with parts separated of the buckle member of FIG. 1.
Figure 3:
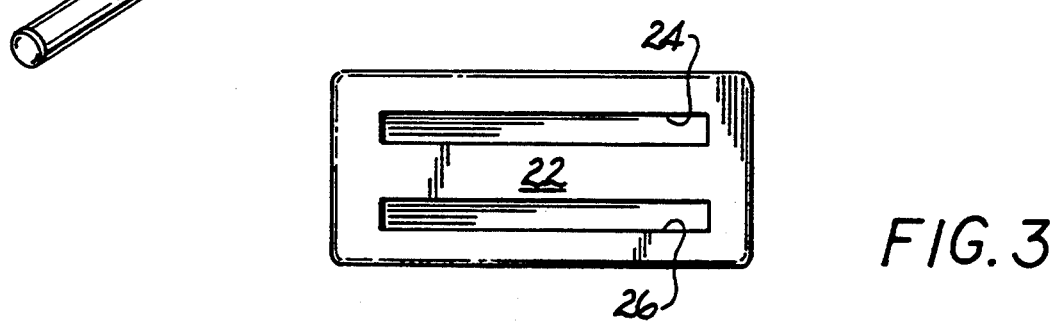
FIG. 3 is a side elevation view of the buckle member of FIG. 1.

Referring initially to FIG. 1, there is illustrated an enlarged perspective view of the strap assembly 10 constructed according to the present invention. Strap assembly 10 has particular application in securing split portions of a sternum together after a sternotomy. However, one skilled in the art will readily appreciate other applications for strap assembly 10.

Strap assembly 10 includes elongated strap 12 and buckle member 14. Strap 12 is preferably readily pliable and may be formed of any material suitable for use in stabilizing fractured bones or securing tissue portions together generally. Typically, strap 12 may be fabricated from a wide variety of monofilament and braided materials both absorbable and non-absorbable. Bioabsorbable materials suitable for this use include polymers and copolymers of lactide, glycolide, dioxanone, caprolactone, trimethylene carbonate and blends thereof, along with various combinations of these materials. Examples of suitable non-absorbable materials include those fabricated from synthetic fibers such as polyesters, polyethylene, polytetrafluoroethylene, polyamides, polycarbonate, polyvinyl chlorides, polypropylenes and polysulfones.

U.S. patent application Ser. No. 07/829,423, filed Feb. 3, 1992, the contents of which are incorporated herein by reference, discloses a strap or sternum closure ribbon which may be readily adapted for use with the strap assembly 10 of the present invention. The strap disclosed in this application is a braided product having a plurality of elongated filamentary reinforcing members of ultra high molecular weight high tenacity polyethylene fibers. These fibers may be plasma treated to reduce slip characteristics of the yarn and exhibit a strength from about 375 kpsi (thousands of pounds per square inch) to about 560 kpsi and a tensile module from about 15 msi (millions of pounds per square inch) to about 30 msi.

U.S. Pat. No. 5,019,093 to Kaplan et al. which issued on May 28, 1991, the contents of which are also incorporated herein by reference, discloses a suture product which may also be adapted for use with the strap assembly 10 of the present invention. The suture product disclosed in this application is of braided construction and is preferably fabricated from a bioabsorbable polymer such as a glycolide or a lactide. This product exhibits perceptibly enhanced flexibility and hand as well as reduced chatter and drag compared with braided sutures of known construction.

Referring now to FIGS. 2-5, buckle 14 is illustrated in detail so as to illustrate the novel securing mechanism of the present invention. Buckle 14 includes frame 16 and clamp 18 rotatably mounted within the frame about transverse axial pin 20. Frame 16 includes transverse sides 22, each side possessing upper and lower openings 24,26 respectively. Openings 24,26 are configured and dimensioned for reception of the end portions of strap 12. Openings 24 define a passageway through which a first end portion of strap 12 may pass within frame 16 between an upper interior surface 28 (FIG. 4) of the frame and clamp 18. Similarly, openings 26 define a lower passageway in which a second end portion of strap 12 is passed through a lower interior surface 30 of frame 16 and clamp 18.

Figure 4:
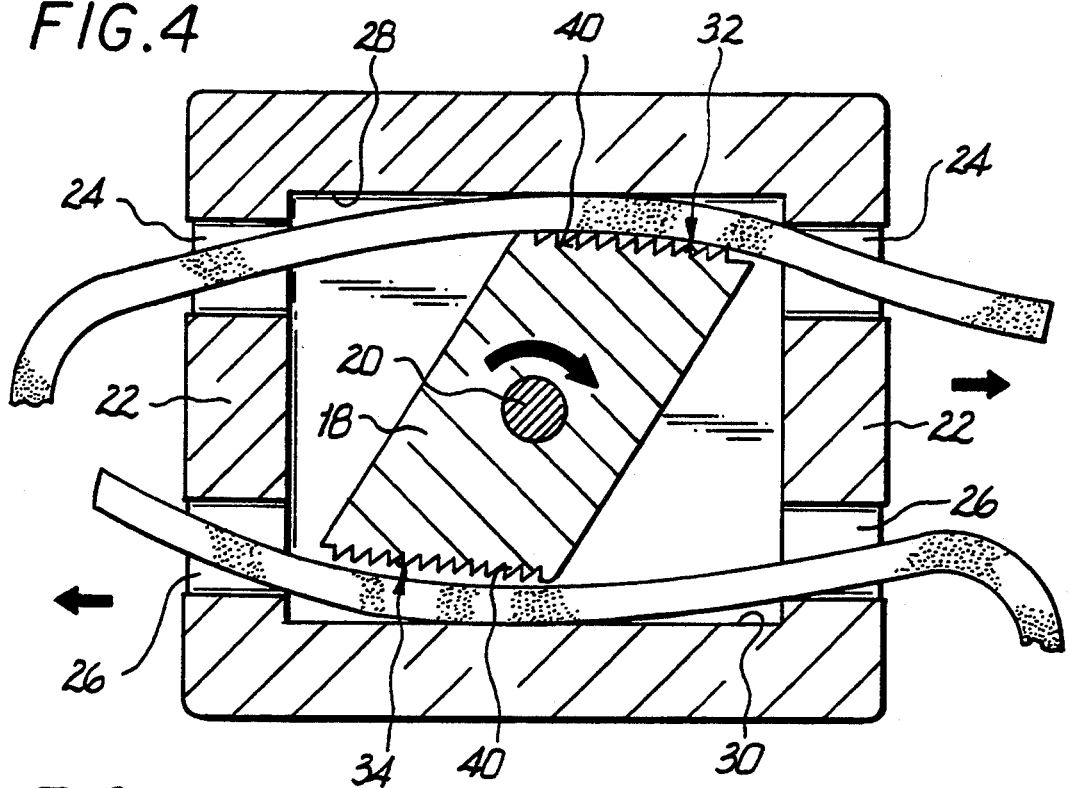
FIG. 4 is a side view in cross-section of the buckle member of FIG. 1 illustrating the non-secured position of the buckle member.
Figure 5:
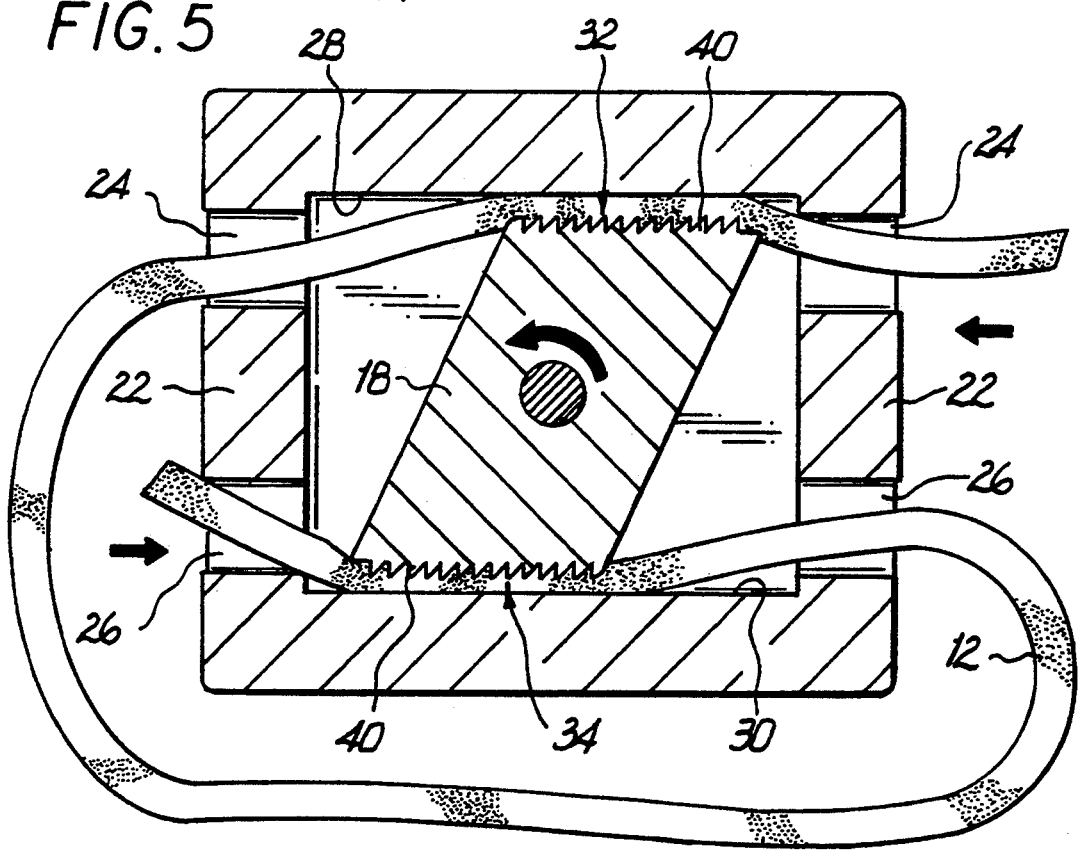
FIG. 5 is a side view in cross-section of the buckle member of FIG. 1 illustrating the secured position of the buckle member with the clamp member securely engaging the strap received within the buckle.

Clamp 18 is adapted for slight rotation about axial pin 20 from an open position (FIG. 4) to permit both ends of strap 12 to pass through frame 16 to a closed position wherein the clamp secures both strap end portions against their respective upper and lower interior surfaces of the frame 16 (FIG. 5). Clamp 18 includes upper and lower wedging surfaces 32,34 respectively, which engage the strap end portions when the clamp member is in the secured position of FIG. 5. Wedging surfaces 32,34 are particularly configured such that a substantial portion of each surface engages the strap end portions when clamp 18 is in the strap securing position.

Wedging surfaces 32,34 preferably each include engaging teeth 40 to facilitate frictional engagement of the strap end portions. Engaging teeth 40 are preferably angularly oriented as shown so as to permit the strap end portions to pass in one direction, i.e., a strap tensioning direction (indicated by the arrows in FIG. 4), while engaging and preventing the strap end portions from passing in a strap loosening direction during tensioning of the strap about the tissue portions.

Clamp 18 rotates to its strap engaging position in response to the tensional forces exerted on strap 12 during tightening thereof about the tissue portions. In particular, as strap 12 is tightened about the tissue portions the strap generates internal reacting forces or clamping forces which oppose the tensional forces exerted on the strap. These reacting forces effect movement of strap 12 towards its unstressed condition, i.e., causing the free ends of the strap to move in a loosening direction, (as indicated by the arrows in FIG. 5) when the strap end portions are released. During this movement, angularly oriented strap engaging teeth 40 of wedging surfaces 32,34 engage and penetrate the strap ends. Further sliding movement of strap ends in the loosening direction causes clamp 18 to rotate slightly in the direction indicated by the arrow in FIG. 5, due to the engagement of teeth 40 with the strap ends, to its secured position. In this position, wedging surfaces 32,34 of the clamp member securely wedge the respective strap end portions against upper and lower interior surfaces 28,30 of frame 16. Thus, it is to be appreciated that the tensional forces exerted on strap 12 during tightening thereof about the sternum effect securement of buckle 14. Generally, the amount of tensional forces needed to generate a clamping force sufficient to maintain clamp 18 in the secured position is minimal.

The components of buckle 14 may be fabricated from a bio-compatible metal such as stainless steel or titanium. Buckle 14 may also comprise synthetic absorbable materials including polymers or copolymers of glycolide, lactide, trimethylene carbonate, lactone, dioxanone, caprolactone or blends thereof or nonabsorbable materials including polycarbonate, polyesters, polyethylene, polyamides, polyvinyl chlorides, polypropylenes, polytetrafluoroethylene, polysulfones, acrylics and polypropylene. It is also within the scope of the present invention for buckle 14 to be fabricated from a combination of such absorbable and non-absorbable materials.

Figure 7:
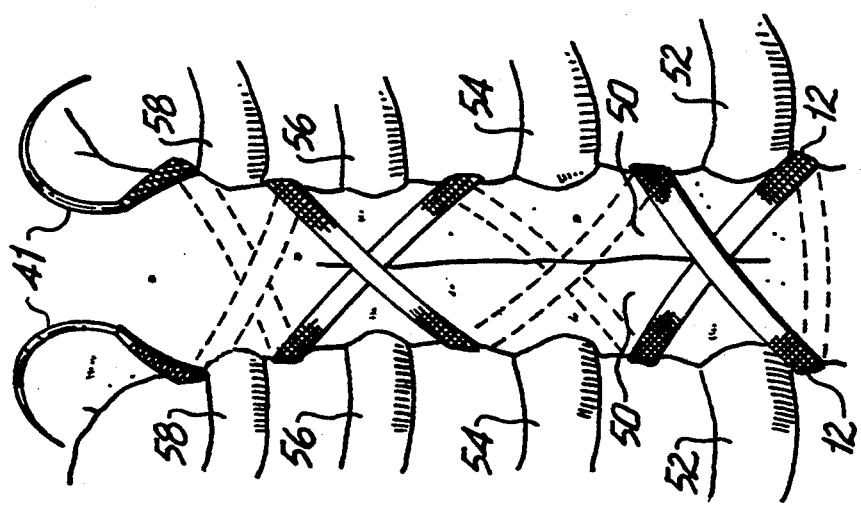

As shown in FIG. 7, strap 12 may have a surgical needle 41 attached at one or both ends thereof to assist in penetrating the targeted parasternal location and passing the strap under the sternum and then outwardly at an opposite parasternal location. A curved needle is appropriate for sternum closure and may be securely attached to strap 12 by conventional methods. The end portions of strap 12, which are to be attached to needle 41, may be tapered to facilitate the needle-attachment process.

Further understanding of the strap assembly 10 of the present invention will be realized from the description provided of the use of same in securing split portions of a sternum together after a sternotomy.

Figure 6:
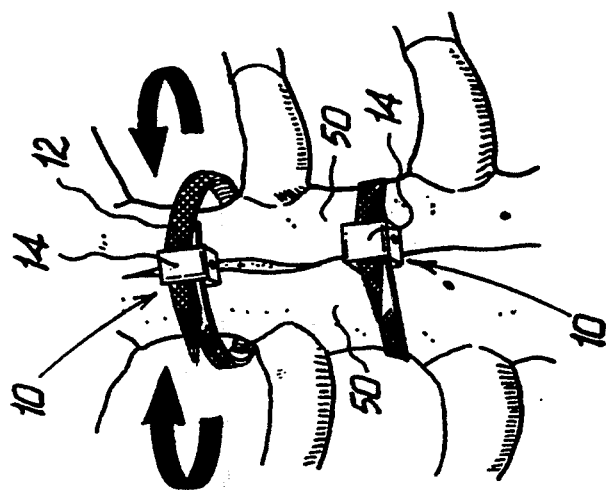
FIG. 6 is a perspective view of the strap assembly of FIG. 1 in a closed looped configuration about the sternum.

FIG. 6 illustrates two strap assemblies positioned about split sternum portions 50. A first strap assembly 10 is shown positioned about an upper section of the sternum, with buckle 14 in the non-secured position. A second strap assembly 10 is shown positioned about a lower section of the sternum, with the buckle 14 in the secured position.

The application of strap assembly 10 around sternum portions 50 to effect sternum closure is accomplished by grasping a first end of strap 12, preferably having a needle attached thereto, and inserting the needle with attached strap through intercostal tissue between adjacent ribs at a first side of the sternum and then maneuvering the needle under both sternum portions 50 to an opposite parasternal location where it is exposed from the intercostal tissue between the ribs at a second side of the sternum. The needle with attached strap 12 is pulled from the sternum location until a sufficient working length of the strap is provided. The needle may then be removed. As best shown in FIG. 4, the first strap end portion is inserted through upper opening 24 in one of transverse sides 22 and passed through frame 16 between upper interior surface 28 and wedging surface 32 of clamp 18. The particular dimensioning of wedging surface 32 and the angular orientation of engaging teeth 40 permit strap 12 to pass through with slight impedance. Thereafter, the second strap end portion is inserted through lower opening 26 in transverse side 22 and passed through frame 16 between lower interior surface 30 and lower wedging surface 34 of clamp 18 in a similar manner. Once both strap end portions are passed through frame 16, the surgeon grasps both strap ends and pulls in an outward, i.e. a tensioning direction as indicated by the arrows in FIG. 4, to remove most of the slack formed in the loop.

At this point in the procedure, strap 12 is not securely tightened around sternum portions 50. One or more strap assemblies may be placed around selected parasternal locations of the sternum in the same manner. When several strap assemblies are in place around the sternum, each strap 12 is tightened by pulling on both strap ends in a tensioning direction. Once strap 12 is tightened about sternum portions 50 to a predetermined desired tension, the strap end portions are released thereby causing engagement with engaging teeth 40 of wedging surfaces 32,34 and rotation of clamp 18 to the strap securing position of FIG. 5. In the secured position, wedging surfaces 32,34 wedge the strap against upper and lower interior surfaces 28,30 of frame 16. The remaining strap assemblies are secured around the sternum in the same manner. Once the strap assemblies are secured in place, the excess working lengths of the strap ends may be removed.

Figure 8:
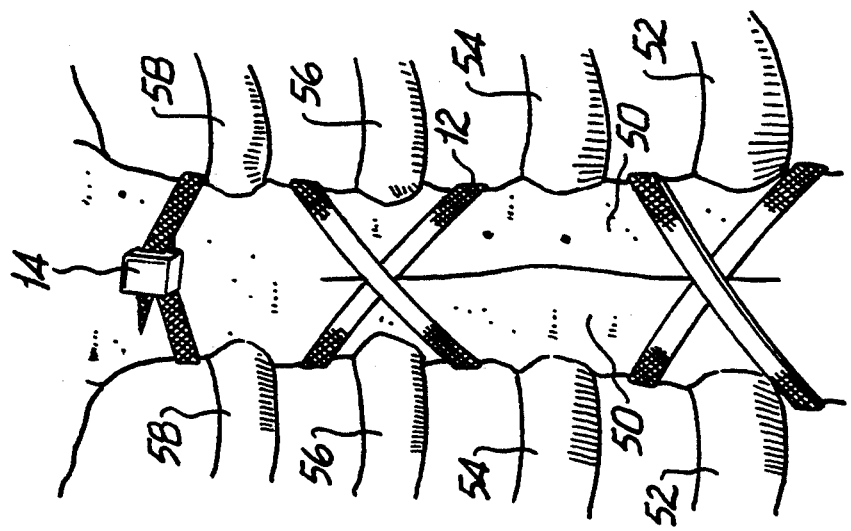
FIGS. 7-8 are perspective views illustrating an alternative method of securing split portions of a sternum with the strap assembly of FIG. 1, in which the strap is looped in a criss-cross manner about the sternum.

Referring now to FIGS. 7–8, an alternative preferred method for repairing split portions of the sternum with the strap assembly 10 of the present invention is illustrated. In accordance with this preferred method, strap 12 is looped about sternum portions 50 in a criss-cross manner through several parasternal locations, and then fastened at one point to a single buckle 14.

Initially, strap 12 is passed through intercostal tissue between a first pair of adjacent rib portions at one side of the sternum, looped about sternum portions 50 to an opposite parasternal location wherein the needle is exposed. Thereafter, the strap end portions are maneuvered in a criss-cross manner such that each end portion may be passed through the intercostal tissue between a next pair of adjacent ribs 52,54. Needles 41 are inserted within the intercostal tissue and maneuvered in a criss-cross manner beneath sternum portions 50 (shown in phantom) so that the strap end portions are crossed over with the strap end portions being proximate a next pair of adjacent ribs 54,56. The needles are exposed and this process is repeated until a desired portion of the sternum is secured. In FIG. 7, strap 12 is crossed over in this manner to secure a sternum portion encompassing four ribs.

The strap securing process is continued by pulling on both strap ends to remove the slack throughout the looped suture. Thereafter, needles 41 are removed and each strap end is inserted within their respective slotted openings 24,26 in frame 16. Strap 12 is then tightened to a predetermined desired tension about the sternum portions 50. The strap end portions are released whereby the tensional forces exerted on the strap transform into a clamping force to drive clamp 18 to its securing position. This novel criss-cross manner of looping and securing strap assembly 10 about the sternum effectively retains the adjacent sternum portions in contacting relation during healing while reducing the number of strap assemblies required to effect sternum closure.

Referring now to FIGS. 9-10, another preferred embodiment of the strap assembly of the present invention is illustrated. In accordance with this embodiment, buckle 60 includes frame 62 and clamp 64. Frame 62 includes upper and lower interior surfaces 66,68 respectively. Surfaces 66,68 possess recesses 70,72, respectively, which are particularly dimensioned to receive wedging surfaces 74,76 of clamp 64 when the buckle is in the strap securing position of FIG. 10. Wedging surfaces 74,76 include teeth 78 to facilitate engagement of strap 12. Teeth 78 are preferably angularly oriented although it is possible for teeth 78 to be generally straight and still maintain an engaged relation with strap 12.

In the secured position of clamp 64, the strap end portions are driven into the respective recesses 70,72 and secured therewithin by wedging surfaces 74,76 of clamp 64. Recesses 70,72 alter the paths in which the strap end portions are received within frame 62, and, as such, impede sliding movement of the strap end portions within the frame thereby facilitating strap securement. Upper and lower surfaces 66,68 also define clamp retaining walls 80,82, respectively, extending generally transversely relative to the strap receiving passageways. Retaining walls 80,82 are dimensioned to prevent clamp 64 from further rotating in response to tension in strap 12 once the clamp has assumed its secured position, thus, retaining the clamp within the recesses 70, 72. Retaining walls 80,82 also assist in wedging strap 12 within the buckle. In all other respects this embodiment is similar to the strap assembly of FIG. 1.

FIG. 11 illustrates another alternative embodiment of the buckle of the strap assembly of the present invention, in which one strap end portion 12a is mounted to a lower portion of frame 84. Strap end 12a may be molded within frame 84 or mounted thereto by conventional means. The free end 12b of the strap is received within a passageway defined by openings 86 in an upper portion of frame 84. Clamp 88 has one wedging surface 90 which engages strap end 12b when the clamp is in a strap securing position. Clamp 88 also possesses engaging pins 92 which extend from wedging surfaces 90. Pins 92 are preferably angularly oriented in a similar manner as the strap engaging teeth of the embodiment of FIGS. 1-5. Pins 92 are adapted to penetrate the strap ends to effect rotational movement of clamp 88 to its secured position and may be mounted to the wedging surfaces by conventional means. Clamp 88 is adapted to slightly rotate from a non-strap securing position to a strap securing position in a similar manner as the clamp of FIG. 1.

While the above description contains many specifics, these specifics should not be construed as limitations on the scope of the invention, but merely as exemplifications of preferred embodiments thereof. Those skilled in the art will envision many other possible variations that are within the scope and spirit of the invention as defined by the claims appended hereto.

What is claimed is:

1. A strap assembly for surgical repair of split portions of a human sternum to retain the sternum portions in adjacent contacting relation during healing, which comprises:
   a strap member dimensioned to be passed through intercostal tissue and about split portions of a sternum, said strap member having first and second end portions; and
   a buckle member dimensioned to be positioned adjacent the sternum, said buckle member comprising:
      means for receiving at least said first end portion of said strap member and for permitting passage of said first end portion through said buckle member; and
      rotatable means within said buckle member for rotating to a strap securing position in response to tensional forces exerted on said strap member during tightening thereof about the sternum portions for securing said strap member in a looped tensioned condition about the split sternum portions, said rotatable means rotatably mounted about a pin disposed within said buckle member.

2. The strap assembly according to claim 1 wherein said strap member comprises nonabsorbable synthetic fibers selected from the group consisting of polycarbonate, polyesters, polyethylene, polyamides, polyvinyl chlorides, polypropylenes, polytetrafluoroethylene and polysulfones.

3. The strap assembly according to claim 1 wherein said strap member comprises bioabsorbable fibers selected from the group consisting of catgut and synthetic materials including polymers and copolymers of lactide, glycolide, dioxanone, caprolactone and trimethylene carbonate.

4. The strap assembly according to claim 1 wherein said buckle member comprises a base member having first and second side walls, said first and second side walls each comprising at least one opening therein, said at least one openings in said first and second sidewalls in general parallel relationship with each other and with a longitudinal passageway extending within said buckle member wherein said first end portion of said strap member is received within said at least one opening of said first sidewall, passed through said longitudinal passageway and extended out of said at least one opening of said second sidewall.

5. The strap assembly according to claim 4 wherein said rotatable means is disposed within said base member of said buckle member and rotatable about an axis in general parallel relationship to a plane defined by said at least one longitudinal passageway.

6. A strap assembly for surgical repair of split portions of tissue to retain the tissue portions in adjacent contacting relation during healing, which comprises:
   a strap member for looping about split portions of tissue and having first and second end portions; and
   buckle means for securing said strap member in a looped tensioned condition about the split tissue portions, said buckle means comprising:
      frame means defining at least one longitudinal passageway extending therethrough for reception and passage of at least said first end portion of said strap member; and
      clamp means rotatably mounted within said frame means and rotatable from a non-strap securing position to a strap securing position in response to tensional forces exerted on said strap member during tensioning thereof about the tissue portions, said clamp means rotatably mounted about a pin disposed within said frame means.

7. The strap assembly according to claim 6 wherein said clamp means defines at least one wedging surface, said at least one wedging surface securely wedging said strap member against a bearing surface of said frame means when said clamp means is in said strap securing position.

8. The strap assembly according to claim 7 further comprising strap engaging means disposed on said at least one wedging surface of said clamp means for facilitating engagement of said strap member.

9. The strap assembly according to claim 8 wherein said strap engaging means is angularly oriented in a manner to permit advancement of said strap member through said at least one passageway in a strap tightening direction while engaging said strap member when said strap member moves through said at least one passageway in a strap loosening direction whereby engagement of said strap member by said strap engagement means during movement of said strap member in the strap loosening direction effects rotational movement of said clamp member to said strap securing position.

10. The strap assembly according to claim 9, wherein said frame means comprises two of said longitudinal passageways, a first of said passageways extending through an upper portion of said frame means to accommodate said first end portion of said strap member, a second of said passageways extending through a lower portion of said frame means to accommodate said second end portion of said strap member wherein said clamp means is disposed between said first and second passageways.

11. The strap assembly according to claim 10 wherein said clamp means comprises two said wedging surfaces, a first of said wedging surfaces securely wedging said first strap end portion against an upper bearing surface of said frame means when said clamp means is in said strap securing position, a second of said wedging surfaces securely wedging said second strap end portion against a lower bearing surface of said frame means when said clamp means is in said strap securing position.

12. The strap assembly according to claim 11 wherein said first and second wedging surfaces each include said strap engaging means.

13. The strap assembly according to claim 9 wherein said strap engaging means comprises engaging teeth formed on said at least one wedging surface.

14. The strap assembly according to claim 9 wherein said strap engaging means comprises a plurality of piercing pin members mounted to said at least one wedging surface.

15. The strap assembly according to claim 7 wherein said bearing surface of said frame means defines a recessed portion.

16. The strap assembly according to claim 15 wherein said clamp means is correspondingly configured and dimensioned such that said at least one wedging surface of said clamp means is received within said recess of said bearing surface when said clamp means is in said strap securing position.

17. The strap assembly according to claim 6 wherein a first end portion of said strap member is mounted to said frame means.

18. The strap assembly according to claim 6 wherein said buckle means comprises nonabsorbable synthetic materials selected from the group consisting of polycarbonate, polyesters, polyethylene, polyamides, polyvinyl chlorides, polypropylenes, polytetrafluoroethylene and polysulfones.

19. The strap assembly according to claim 6 wherein said buckle means comprises steel.

20. The strap assembly according to claim 6 wherein said buckle means comprises titanium.

21. The strap assembly according to claim 6 wherein said clamp means is rotatable about an axis disposed in a plane which is in general parallel relationship to a plane defined by said at least one longitudinal passageway.

22. A strap assembly for surgical repair of split portions of tissue to retain the tissue portions in adjacent contacting relation during healing, which comprises:
a strap member; and
buckle means for securing said strap member in a looped tensioned condition about the split tissue portions, said buckle means comprising:
frame means including at least one longitudinal passageway for reception of said strap member and a bearing surface having a recessed portion, said recessed portion defining a retaining surface extending generally transversely from said bearing surface; and
clamp means rotatably mounted within said frame means, said clamp means rotatable from a non-strap securing position to a strap securing position in response to tensional forces exerted on said strap member during tensioning thereof about the tissue portions, said clamp means defining at least one wedging surface, said at least one wedging surface securely wedging said strap member against said bearing surface of said frame means when said clamp means is in said strap securing position;
wherein when in said strap securing position of said clamp means said at least one wedging surface is received within said recessed portion of said frame means such that said clamp means is retained in said strap securing position by engagement of at least a portion of said clamp means with said transverse retaining surface defined by said recessed portion.

23. A strap assembly to be looped about split portions of tissue to retain the portions in adjacent engaged relation to promote healing thereof, which comprises:
a flexible strap member for looping about split tissue portions and having first and second end portions; and
a buckle member including:
a frame having a first longitudinal passageway extending therethrough for reception and passage of said first strap end portion and a second longitudinal passageway extending therethrough for reception and passage of said second strap end portion; and
a clamp member disposed between said first and second passageways and rotatably mounted within said frame, said clamp member rotatable from a non-strap securing position to a strap securing position, said clamp member securely engaging said first and second strap end portions when in said strap securing position to retain said strap member in a looped tensioned condition about the tissue portions.

24. A strap assembly for surgical repair of split portions of tissue to retain the tissue portions in adjacent contacting relation during healing, which comprises:
a strap member having first and second end portions; and
a buckle member for securing said strap member in a looped tensioned condition about the split tissue portions, said buckle member including:
a frame member defining first and second generally longitudinal extending channels, said first channel for reception of said first strap end portion, said second channel for reception of said second strap end portion; and
a clamp member disposed within said frame member and having first and second end portions, said clamp member rotatably mounted about an axis of rotation disposed intermediate said first and second end portions of said clamp member and rotatable to a strap securing position in response to tensional forces exerted on said strap member, wherein in said strap securing position said first end portion of said clamp member securely wedges said first strap end portion against a first bearing surface of said frame member and said second end portion of said clamp member securely wedges said second strap end portion against a second bearing surface of said frame member.

25. A strap assembly for surgical repair of split portions of tissue to retain the tissue portions in adjacent contacting relation during healing, which comprises:
a strap member for looping about split portions of tissue and having first and second end portions; and
a buckle member for securing said strap member in a looped tensioned condition about the split tissue portions, said buckle member comprising:
a frame member defining two longitudinal passageways, a first of said passageways extending through an upper portion of said frame member to accommodate said first end portion of said strap member, a second of said passageways extending through a lower portion of said frame member to accommodate said second end portion of said strap member; and
a clamp member rotatably mounted within said frame means and having first and second wedging surfaces, said clamp member rotatable from a non-strap securing position to a strap securing position in response to tensional forces exerted on said strap member during tensioning thereof about the tissue portions, wherein in said strap securing position said first wedging surface securely wedges said first strap end portion against a first bearing surface of said frame member and said second wedging surface securely wedges said second strap end portion against a second bearing surface of said frame member.

26. A method for repairing split portions of tissue, comprising the steps of:
providing a strap assembly including a strap member having first and second end portions and buckle means attached to said first end portion of said strap member, said buckle means including frame means defining at least one longitudinal passageway for reception of said strap member and clamp means rotatably mounted within said frame means about a pin, said clamp means rotatable from a non-strap securing position to a strap securing position in response to the tensional forces exerted on said strap member during tensioning thereof about the tissue portions;
looping said strap member around the tissue portions;
inserting said second end portion of said strap member through said at least one passageway in said buckle member;
tightening the looped strap member about the tissue portions in a manner to attach the tissue portions in an adjacent engaged relation; and
securing said strap member to said buckle member.

27. A method for securing first and second portions of a sternum to retain the portions in adjacent engaged relation during healing, comprising the steps of:
a) providing at least one strap assembly comprising a flexible strap member having first and second end portions and a buckle member, said buckle member including a frame having a first longitudinal passageway disposed in an upper portion thereof for accommodating said first strap end portion and a second longitudinal passageway disposed in a lower portion thereof for accommodating said second strap end portion, said buckle member further including a clamp member rotatably mounted within said frame for rotating from a non-strap securing position to a strap securing position;
b) looping said strap member about the sternum portions and through intercostal tissue disposed between a first pair of adjacent ribs;
c) maneuvering said first and second end portions of said strap member in a criss-cross manner about the sternum portions such that each said end portions passes through intercostal tissue disposed between a pair of next adjacent ribs;
d) repeating step (c) as desired until a predetermined section of the sternum is enclosed by said strap member;
e) inserting said first end portion of said looped strap member in said first passageway of said frame;
f) inserting said second end portion of said looped strap member in said second passageway of said frame;
g) tightening said looped strap member about the sternum portions in a manner to attach the tissue portions in adjacent engaged relation; and
h) securing said strap member within said buckle member.

* * * * *